United States Patent
Schwartz et al.

(10) Patent No.: US 9,402,929 B2
(45) Date of Patent: ***Aug. 2, 2016

(54) DECONTAMINATION SYSTEM INCLUDING ENVIRONMENTAL CONTROL USING A DECONTAMINATING SUBSTANCE

(71) Applicant: Medivators Inc., Minneapolis, MN (US)

(72) Inventors: Mason Schwartz, Elk River, MN (US); Jonathan K. Olson, Delano, MN (US)

(73) Assignee: MAR COR PURIFICATION, INC., Skippak, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/672,859

(22) Filed: Mar. 30, 2015

(65) Prior Publication Data

US 2015/0202339 A1  Jul. 23, 2015

Related U.S. Application Data

(63) Continuation of application No. 13/478,837, filed on May 23, 2012, now Pat. No. 9,017,607.

(60) Provisional application No. 61/490,813, filed on May 27, 2011.

(51) Int. Cl.
  *A61L 2/24* (2006.01)
  *A61L 2/20* (2006.01)
  *A61L 2/22* (2006.01)

(52) U.S. Cl.
  CPC ... *A61L 2/22* (2013.01); *A61L 2/20* (2013.01); *A61L 2/208* (2013.01); *A61L 2/24* (2013.01)

(58) Field of Classification Search
  CPC ............. A61L 2/20; A61L 2/208; A61L 2/22; A61L 2/24
  USPC .................................................. 422/28, 30, 33
  See application file for complete search history.

(56) References Cited

U.S. PATENT DOCUMENTS 1,062,404 A   5/1913  Kiefer
1,114,880 A   10/1914  Hall
(Continued)

FOREIGN PATENT DOCUMENTS

CN   1141003 A   1/1997
CN   1585817 A   2/2005
(Continued)

OTHER PUBLICATIONS

"Cantel Subsidiary Receives Expanded EPO Approval for Minncare Cold Sterilant in Fogging Applications", Business Wire, Jul. 4, 2008, 1 page.
(Continued)

*Primary Examiner* — Sean E Conley
*Assistant Examiner* — Donald Spamer
(74) *Attorney, Agent, or Firm* — Faegre Baker Daniels LLP

(57) ABSTRACT

A system for decontaminating a device, such as a medical device, includes a decontamination chamber configured to retain the device and a chemical dispersion assembly configured to deliver a decontaminating fluid to the decontamination chamber. A pressure control assembly is connected to the decontamination chamber and configured to control the pressure in the decontamination chamber. The system also includes a system controller configured to control the decontamination chamber, chemical dispersion assembly, and pressure control assembly. A decontaminating fluid is added into the decontamination chamber at a first rate while increasing the pressure in the decontamination chamber. Adding the decontaminating fluid increases a relative humidity in the decontamination chamber.

18 Claims, 3 Drawing Sheets

(56) References Cited

U.S. PATENT DOCUMENTS

| | | |
|---|---|---|
| 1,837,264 A | 12/1931 | Hackley |
| 2,965,936 A | 6/1957 | Kaye |
| 2,836,570 A | 5/1958 | Peers |
| 3,114,599 A | 12/1963 | Fanning |
| 3,436,173 A | 4/1969 | Power |
| 3,498,742 A | 3/1970 | Long |
| 3,547,576 A | 12/1970 | Sheikh |
| 3,816,074 A | 6/1974 | Decupper |
| 3,936,270 A | 2/1976 | Gunther |
| 3,958,935 A | 5/1976 | Kowol |
| 4,064,062 A | 12/1977 | Yurko |
| 4,119,400 A | 10/1978 | Kurz |
| 4,169,123 A | 9/1979 | Moore et al. |
| 4,169,124 A | 9/1979 | Forstrom et al. |
| 4,230,663 A | 10/1980 | Forstrom et al. |
| 4,241,010 A | 12/1980 | Baran |
| 4,241,020 A | 12/1980 | Grantham |
| 4,249,265 A | 2/1981 | Coester |
| 4,259,103 A | 3/1981 | Malek et al. |
| 4,270,658 A | 6/1981 | Schuster |
| 4,294,804 A | 10/1981 | Baran |
| 4,366,125 A | 12/1982 | Kodera et al. |
| 4,447,399 A | 5/1984 | Runnells et al. |
| 4,457,892 A | 7/1984 | Young |
| 4,483,771 A | 11/1984 | Koch |
| 4,512,951 A | 4/1985 | Koubek |
| 4,587,264 A | 5/1986 | Jourdan-Laforte et al. |
| 4,592,896 A | 6/1986 | Runnells et al. |
| 4,637,916 A | 1/1987 | Hennebert et al. |
| 4,643,876 A | 2/1987 | Jacobs et al. |
| 4,687,635 A | 8/1987 | Kaehler et al. |
| 4,744,951 A | 5/1988 | Cummings et al. |
| 4,756,882 A | 7/1988 | Jacobs et al. |
| 4,843,867 A | 7/1989 | Cummings |
| 4,892,705 A | 1/1990 | Sternfeld et al. |
| 4,904,901 A | 2/1990 | Simopoulos et al. |
| 4,921,675 A | 5/1990 | Johnson |
| 4,943,414 A | 7/1990 | Jacobs et al. |
| 4,952,370 A | 8/1990 | Cummings et al. |
| 4,956,145 A | 9/1990 | Cummings et al. |
| 4,986,963 A | 1/1991 | Corcoran et al. |
| 5,008,079 A | 4/1991 | Wltzler et al. |
| 5,258,162 A | 11/1993 | Andersson et al. |
| 5,340,878 A | 8/1994 | Sadatoshi et al. |
| 5,460,962 A | 10/1995 | Kemp |
| 5,482,683 A | 1/1996 | Sheth et al. |
| 5,508,009 A | 4/1996 | Rickloff et al. |
| 5,512,244 A | 4/1996 | Griffiths et al. |
| 5,527,508 A | 6/1996 | Childers et al. |
| 5,534,221 A | 7/1996 | Hillebrenner et al. |
| 5,556,607 A | 9/1996 | Childers et al. |
| 5,580,530 A | 12/1996 | Kowatsch et al. |
| 5,620,656 A | 4/1997 | Wensky et al. |
| 5,641,455 A | 6/1997 | Rosenlund et al. |
| 5,667,753 A | 9/1997 | Jacobs et al. |
| 5,674,450 A | 10/1997 | Lin et al. |
| 5,676,837 A | 10/1997 | Jungbauer et al. |
| 5,733,503 A | 3/1998 | Kowatsch et al. |
| 5,741,460 A | 4/1998 | Jacob et al. |
| 5,779,973 A | 7/1998 | Edwards et al. |
| 5,784,934 A | 7/1998 | Izumisawa |
| 5,792,422 A | 8/1998 | Lin et al. |
| 5,801,010 A | 9/1998 | Falkowski et al. |
| 5,834,313 A | 11/1998 | Lin |
| 5,847,393 A | 12/1998 | Van Den Berg et al. |
| 5,851,483 A | 12/1998 | Nicolle et al. |
| 5,863,499 A | 1/1999 | Kralovic |
| 5,869,000 A | 2/1999 | DeCato |
| 5,876,666 A | 3/1999 | Lin et al. |
| D408,837 S | 4/1999 | Gotham et al. |
| 5,902,413 A | 5/1999 | Puszko et al. |
| 5,904,901 A | 5/1999 | Shimono et al. |
| 5,906,794 A | 5/1999 | Childers |
| 5,955,025 A | 9/1999 | Barrett |
| 5,961,921 A | 10/1999 | Addy et al. |
| 5,980,825 A | 11/1999 | Addy et al. |
| 6,010,662 A | 1/2000 | Lin et al. |
| 6,030,579 A | 2/2000 | Addy et al. |
| 6,036,918 A | 3/2000 | Kowanko |
| 6,039,922 A | 3/2000 | Swank et al. |
| 6,041,794 A | 3/2000 | Lin et al. |
| 6,066,294 A | 5/2000 | Lin et al. |
| 6,094,887 A | 8/2000 | Swank et al. |
| 6,096,265 A | 8/2000 | Mezger et al. |
| 6,096,266 A | 8/2000 | Duroselle |
| 6,120,730 A | 9/2000 | Swank et al. |
| 6,135,433 A | 10/2000 | Nurmi |
| 6,162,394 A | 12/2000 | Nicolle et al. |
| 6,162,395 A | 12/2000 | Kowanko |
| 6,183,691 B1 | 2/2001 | Swank et al. |
| D438,980 S | 3/2001 | Hehenberger |
| 6,234,310 B1 | 5/2001 | Goldhaber |
| 6,269,680 B1 | 8/2001 | Prieve et al. |
| 6,286,527 B1 | 9/2001 | Stanley |
| 6,312,645 B1 | 11/2001 | Lin et al. |
| 6,312,646 B2 | 11/2001 | Kowanko |
| 6,354,312 B1 | 3/2002 | Lin et al. |
| 6,365,102 B1 | 4/2002 | Wu et al. |
| 6,365,103 B1 | 4/2002 | Fournier |
| 6,391,260 B1 | 5/2002 | Davis et al. |
| 6,406,666 B1 | 6/2002 | Cicha et al. |
| 6,439,246 B2 | 8/2002 | Stanley |
| 6,451,254 B1 | 9/2002 | Wang et al. |
| 6,468,472 B1 | 10/2002 | Yu et al. |
| 6,495,100 B1 | 12/2002 | Lin et al. |
| 6,528,017 B2 | 3/2003 | Jacobs et al. |
| 6,530,399 B2 | 3/2003 | Nguyen et al. |
| 6,582,654 B1 | 6/2003 | Kral et al. |
| 6,594,971 B1 | 7/2003 | Addy et al. |
| 6,596,231 B1 | 7/2003 | Catelli et al. |
| 6,600,444 B2 | 7/2003 | Desjardins |
| 6,641,781 B2 | 11/2003 | Walta |
| 6,673,313 B2 | 1/2004 | Wang et al. |
| 6,746,647 B2 | 6/2004 | Kohler et al. |
| 6,790,410 B2 | 9/2004 | Metzner et al. |
| 6,797,234 B2 | 9/2004 | Stanley |
| 6,884,392 B2 | 4/2005 | Malkin et al. |
| 6,977,061 B2 | 12/2005 | Lin et al. |
| 6,998,582 B1 | 2/2006 | Maroti |
| 7,001,873 B2 | 2/2006 | McDonnell et al. |
| 7,005,549 B2 | 2/2006 | Hobson et al. |
| 7,025,932 B2 | 4/2006 | Martin et al. |
| 7,146,746 B2 | 12/2006 | Kawasaki |
| 7,178,555 B2 | 2/2007 | Engel et al. |
| 7,179,419 B2 | 2/2007 | Lin et al. |
| 7,186,371 B1 | 3/2007 | Watling |
| 7,186,372 B2 | 3/2007 | Kohler et al. |
| 7,186,374 B2 | 3/2007 | Zelina et al. |
| 7,294,305 B2 | 11/2007 | Lin et al. |
| 7,303,073 B2 | 12/2007 | Raynal-Olive et al. |
| 7,307,191 B2 | 12/2007 | Hobson et al. |
| 7,326,382 B2 | 2/2008 | Adiga et al. |
| 7,434,372 B2 | 10/2008 | Vanhamel et al. |
| 7,449,145 B2 | 11/2008 | Kohler et al. |
| 7,452,504 B2 | 11/2008 | Wu et al. |
| 7,468,159 B2 | 12/2008 | Lin et al. |
| 7,491,371 B2 | 2/2009 | Moller et al. |
| 7,541,002 B2 | 6/2009 | Centanni |
| 7,556,767 B2 | 7/2009 | Lin et al. |
| 7,569,180 B2 | 8/2009 | Kohler et al. |
| 7,578,969 B2 | 8/2009 | Mielnik et al. |
| 7,604,773 B2 | 10/2009 | Ekstrom et al. |
| 7,608,218 B2 | 10/2009 | Fryer et al. |
| 7,611,667 B2 | 11/2009 | Centanni |
| 7,615,187 B2 | 11/2009 | Helton et al. |
| 7,622,074 B2 | 11/2009 | Mielnik |
| 7,651,667 B2 | 1/2010 | McVey et al. |
| 7,670,550 B2 | 3/2010 | Lin et al. |
| 7,670,565 B2 | 3/2010 | McVey et al. |
| 7,678,339 B2 | 3/2010 | Wira |
| 7,713,473 B2 | 5/2010 | Kendall et al. |
| 7,718,122 B2 | 5/2010 | Smith et al. |
| 7,803,315 B2 | 9/2010 | McDonnell et al. |
| 7,807,100 B2 | 10/2010 | Choperena et al. |

(56) References Cited

U.S. PATENT DOCUMENTS

| | | |
|---|---|---|
| 7,811,531 B2 | 10/2010 | Mielnik et al. |
| 7,850,925 B2 | 12/2010 | Centanni et al. |
| 7,988,911 B2 | 8/2011 | Centanni et al. |
| 7,988,920 B2 | 8/2011 | Centanni et al. |
| 7,993,602 B2 | 8/2011 | Moriyama et al. |
| 8,012,424 B2 | 9/2011 | Jethrow et al. |
| 8,025,848 B2 | 9/2011 | McVey et al. |
| 3,056,719 A1 | 11/2011 | Porret, Jean-Yves et al. |
| 8,062,590 B1 | 11/2011 | Ricciardi et al. |
| 8,110,156 B2 | 2/2012 | Ricciardi et al. |
| 8,128,789 B2 | 3/2012 | Hirata et al. |
| 8,133,437 B2 | 3/2012 | Scalzo et al. |
| 8,178,357 B2 | 5/2012 | Trogler et al. |
| 8,236,240 B2 | 8/2012 | Childers et al. |
| 8,298,482 B2 | 10/2012 | Rees et al. |
| 8,343,422 B2 | 1/2013 | Sato et al. |
| 8,343,437 B2 | 1/2013 | Patel |
| 8,357,331 B2 | 1/2013 | McVey et al. |
| 8,425,837 B2 | 4/2013 | Carbone et al. |
| 8,444,919 B2 | 5/2013 | Erickson |
| 8,821,807 B2 | 9/2014 | Schwartz et al. |
| 8,889,081 B2 | 11/2014 | Schwartz et al. |
| 9,017,607 B2 | 4/2015 | Olson et al. |
| 2001/0000227 A1 | 4/2001 | Kowanko |
| 2001/0036422 A1 | 11/2001 | Lin et al. |
| 2001/0053333 A1 | 12/2001 | Messier et al. |
| 2002/0069616 A1 | 6/2002 | Odell et al. |
| 2002/0081228 A1 | 6/2002 | Hui et al. |
| 2002/0085950 A1 | 7/2002 | Robitaille et al. |
| 2002/0114727 A1 | 8/2002 | McVey et al. |
| 2002/0122744 A1 | 9/2002 | Hui et al. |
| 2002/0168289 A1 | 11/2002 | McVey |
| 2002/0187067 A1 | 12/2002 | Lukasik et al. |
| 2003/0017074 A1 | 1/2003 | Wang et al. |
| 2003/0086820 A1* | 5/2003 | McDonnell ......... A61K 31/327 422/28 |
| 2003/0124026 A1 | 7/2003 | Williams et al. |
| 2003/0133834 A1 | 7/2003 | Karle |
| 2003/0138347 A1 | 7/2003 | Lin |
| 2003/0190253 A1 | 10/2003 | Kohler et al. |
| 2003/0235511 A1 | 12/2003 | Jacobs et al. |
| 2004/0001776 A1 | 1/2004 | Fryer et al. |
| 2004/0005240 A1 | 1/2004 | Adiga et al. |
| 2004/0005259 A1 | 1/2004 | Sacca |
| 2004/0022671 A1 | 2/2004 | Malatesta |
| 2004/0022673 A1 | 2/2004 | Protic |
| 2004/0028556 A1 | 2/2004 | Frost et al. |
| 2004/0052679 A1 | 3/2004 | Root et al. |
| 2004/0081601 A1 | 4/2004 | Morrissey et al. |
| 2004/0162228 A1 | 8/2004 | Hobson et al. |
| 2004/0170527 A1 | 9/2004 | Jacobs et al. |
| 2004/0184950 A1 | 9/2004 | McVey et al. |
| 2005/0013726 A1 | 1/2005 | Hill et al. |
| 2005/0042130 A1 | 2/2005 | Lin et al. |
| 2005/0084431 A1 | 4/2005 | Hill et al. |
| 2005/0147527 A1 | 7/2005 | Brown et al. |
| 2005/0196313 A1 | 9/2005 | Choperena et al. |
| 2005/0252274 A1 | 11/2005 | Centanni |
| 2005/0260097 A1 | 11/2005 | Williams et al. |
| 2006/0078459 A1 | 4/2006 | Kohler et al. |
| 2006/0088441 A1 | 4/2006 | Hill |
| 2006/0099106 A1 | 5/2006 | Watling et al. |
| 2007/0003431 A1 | 1/2007 | Kendall et al. |
| 2007/0014691 A1 | 1/2007 | Jacobs et al. |
| 2007/0034095 A1 | 2/2007 | McDonnell et al. |
| 2007/0053813 A1 | 3/2007 | Martin |
| 2007/0092398 A1 | 4/2007 | McDonald |
| 2007/0098592 A1 | 5/2007 | Buczynski et al. |
| 2007/0160491 A1 | 7/2007 | Kohler et al. |
| 2007/0207054 A1 | 9/2007 | Langford |
| 2007/0253859 A1 | 11/2007 | Hill |
| 2008/0240981 A1 | 10/2008 | Berentsveig et al. |
| 2009/0209031 A1 | 8/2009 | Stopek |
| 2009/0324445 A1 | 12/2009 | Kohler et al. |
| 2010/0011823 A1 | 1/2010 | Dahms et al. |
| 2010/0028200 A1 | 2/2010 | Shiosawa |
| 2010/0034697 A1 | 2/2010 | Weinberger et al. |
| 2010/0034707 A1 | 2/2010 | Mielnik et al. |
| 2010/0143218 A1 | 6/2010 | Nurminen et al. |
| 2010/0196197 A1 | 8/2010 | Rovison, Jr. et al. |
| 2010/0226821 A1 | 9/2010 | Ricciardi et al. |
| 2010/0296969 A1 | 11/2010 | Ngo et al. |
| 2010/0297776 A1 | 11/2010 | Trogler et al. |
| 2010/0303671 A1 | 12/2010 | Bertrand |
| 2010/0316527 A1 | 12/2010 | McLaren et al. |
| 2011/0044851 A1 | 2/2011 | Centanni et al. |
| 2011/0044852 A1 | 2/2011 | Ryan et al. |
| 2011/0052449 A1 | 3/2011 | Centanni et al. |
| 2011/0076189 A1 | 3/2011 | McVey et al. |
| 2011/0076192 A1 | 3/2011 | Robitaille et al. |
| 2011/0079525 A1 | 4/2011 | Peck et al. |
| 2011/0091354 A1 | 4/2011 | Schwartz et al. |
| 2011/0135537 A1 | 6/2011 | Schwartz et al. |
| 2011/0165299 A1 | 7/2011 | Sato et al. |
| 2011/0182772 A1 | 7/2011 | Holt |
| 2012/0009085 A1 | 1/2012 | Burger |
| 2012/0189494 A1 | 7/2012 | Rovison, Jr. et al. |
| 2012/0219456 A1 | 8/2012 | Childers et al. |
| 2012/0277662 A1 | 11/2012 | Golkowski |
| 2012/0301356 A1 | 11/2012 | Olson et al. |
| 2013/0065958 A1 | 3/2013 | Dunn |
| 2013/0101462 A1 | 4/2013 | Keil |
| 2014/0369887 A1 | 12/2014 | Schwartz et al. |
| 2015/0064066 A1 | 3/2015 | Schwartz et al. |

FOREIGN PATENT DOCUMENTS

| | | |
|---|---|---|
| CN | 102018966 B | 4/2011 |
| CN | 103702689 A | 4/2014 |
| EP | 0302420 A2 | 2/1989 |
| EP | 0774263 A1 | 5/1997 |
| EP | 0923951 B1 | 6/1999 |
| EP | 0923951 B1 | 1/2003 |
| EP | 1378253 A1 | 1/2004 |
| EP | 1481692 B1 | 12/2004 |
| EP | 1813220 A1 | 8/2007 |
| EP | 1473044 B1 | 12/2007 |
| EP | 1171368 B1 | 2/2008 |
| EP | 1935515 A2 | 6/2008 |
| EP | 1308173 B1 | 12/2008 |
| EP | 1110557 B1 | 3/2009 |
| EP | 2228076 A1 | 9/2010 |
| EP | 2714101 A1 | 4/2014 |
| EP | 2506884 B1 | 2/2015 |
| JP | 08126605 A | 5/1996 |
| JP | H08126605 A | 5/1996 |
| JP | 11015570 A | 1/1999 |
| JP | 11137650 A | 5/1999 |
| JP | H11137650 A | 5/1999 |
| JP | 2002508219 A | 3/2002 |
| JP | 2003260118 A | 9/2003 |
| JP | 2005143669 A | 6/2005 |
| JP | 2007167546 A | 7/2007 |
| JP | 2009513213 A | 4/2009 |
| JP | 2009131296 A | 6/2009 |
| JP | 2009268466 A | 11/2009 |
| WO | WO0207788 A1 | 1/2002 |
| WO | WO0249682 A1 | 6/2002 |
| WO | 2006013089 A1 | 2/2006 |
| WO | WO2007008205 A1 | 1/2007 |
| WO | WO2007049076 A1 | 5/2007 |
| WO | WO2008014615 A1 | 2/2008 |
| WO | WO2012128734 A1 | 9/2012 |
| WO | 2012173756 A1 | 12/2012 |

OTHER PUBLICATIONS

"Cantel Subsidiary Receives Expanded EPO Approval for Minncare Cold Sterilant in Fogging Applications", Business Nire, Jul. 4, 2008, 1 page.

(56) References Cited

OTHER PUBLICATIONS

"Vapor Liquid-/Solid System", Retrieved from Internet electronic mail: http:blowers.chee.arizona.edu/201project/Glsys.interrelatn.pgl.HTML/, retrieved on Dec. 10, 2014, Vapor-Liquid/Solid Equilibruim, (C) 2007, 8 pages.
European Search Report issued in EP Application No. 13152441, mailed Feb. 27, 2013, 8 pages.
FMC Material Safety Data Sheet, Date Approved Nov. 10, 2006, 11 pages.
International Preliminary Report on Patentability issued in PCT/US2012/039160, mailed Dec. 12, 2013, 7 pages.
International Search Report and Written Opinion issued in PCT/US2010/052622, mailed Jan. 20, 2011, 14 pages.
International Search Report and Written Opinion issued in PCT/US2010/058885, mailed Feb. 10, 2011, 11 pages.
International Search Report and Written Opinion issued in PCT/US2012/039160, mailed Oct. 2, 2012, 10 pages.
International Standard, ISO 11140-1, 2nd Edition Jul. 15, 2005, Sterilization of Health Care Products—Chemical Indicators—Part 1: General Requirements, pp. 1-27.
Lunger, Mj et al., "Reducing Pump-Down Time With Dry Air Venting", 43rd Annual Technical Conference Proceedings, Denver, Apr. 15-20, 2000, 1 page.
Minncare Dry Fog™ System: An Integral part of Modem Cleanroom Disinfection Procedures, ©2009 Mar Cor Purification, 4 pages.
Portner, Dorothy M. et al., "Sporicidal Effect of Peracetic Acid Vapor", Applied Microbiology, vol. 16, No. 11, Nov. 1968, pp. 1782-1785.
Rutala, William A. et al., "New Disinfection and Sterilization Methods", Emerging Infectious Diseases Journal, vol. 7, No. 2, Mar-Apr 2001, 14 pages.
The Mini Fog System: A Modern Method to Enhance Small Space Disinfection, ©2008 Mar Cor Purification, 2 pages.

\* cited by examiner

DECONTAMINATION SYSTEM INCLUDING ENVIRONMENTAL CONTROL USING A DECONTAMINATING SUBSTANCE

CROSS-REFERENCE TO RELATED APPLICATION

This application is a continuation of U.S. patent application Ser. No. 13/478,837, filed May 23, 2012, entitled "Decontamination System Including Environmental Control Using a Decontamination Substance," which claims the benefit under 35 U.S.C. §119(e) of U.S. Provisional Patent Application 61/490,813 entitled "Decontamination System Including Environmental Control Using a Decontaminating Substance," which are hereby incorporated by reference in their entirety.

TECHNICAL FIELD

The present invention relates to decontamination of medical devices. More particularly, the present invention relates to a system for decontaminating a medical device in a sterilization chamber with an environment at least partially controlled by the components of the decontaminating substance.

BACKGROUND

Robust medical equipment is often sterilized at high temperatures. Commonly, the equipment is sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Further, endoscopes in particular present problems in that such devices typically have numerous exterior crevices and interior lumens which can harbor microbes. The employment of a fast-acting yet gentler sterilization method is desirable for reprocessing sensitive instruments such as endoscopes. Other medical or dental instruments which comprise lumens, crevices, and the like are also in need of methods of cleaning and decontaminating which employ an effective reprocessing system which will minimize harm to sensitive components and materials.

SUMMARY

In one aspect, the present invention relates to a system for decontaminating a device. The system includes a decontamination chamber configured to retain the device and a chemical dispersion assembly configured to deliver a decontaminating fluid to the decontamination chamber. A pressure control assembly is connected to the decontamination chamber and configured to control the pressure in the decontamination chamber. The system also includes a system controller configured to control the decontamination chamber, chemical dispersion assembly, and pressure control assembly. A decontaminating fluid is added into the decontamination chamber at a first rate while increasing the pressure in the decontamination chamber. Adding the decontaminating fluid increases a relative humidity in the decontamination chamber. The decontaminating fluid is then added into the decontamination chamber at a second rate higher than the first rate while increasing the pressure in the decontamination chamber to about within a hold pressure range. After holding the decontaminating fluid in the decontamination chamber for a hold time within the hold pressure range, the decontaminating fluid is evacuated from the decontamination chamber in a decontaminating fluid evacuation step. The decontamination chamber is then vented to atmospheric pressure.

In another aspect, the present invention relates to a method for decontaminating a device in a decontamination chamber. A decontaminating fluid is added into the decontamination chamber at a first rate while increasing the pressure in the decontamination chamber. Adding the decontaminating fluid increases a relative humidity in the decontamination chamber. While increasing the pressure in the decontamination chamber to within a hold pressure range, the decontaminating fluid is added into the decontamination chamber at a second rate higher than the first rate. The decontaminating fluid is held in the decontamination chamber for a hold time within the hold pressure range, and the decontaminating fluid is subsequently evacuated from the decontamination chamber in a decontaminating fluid evacuation step. The decontamination chamber is then vented to atmospheric pressure.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
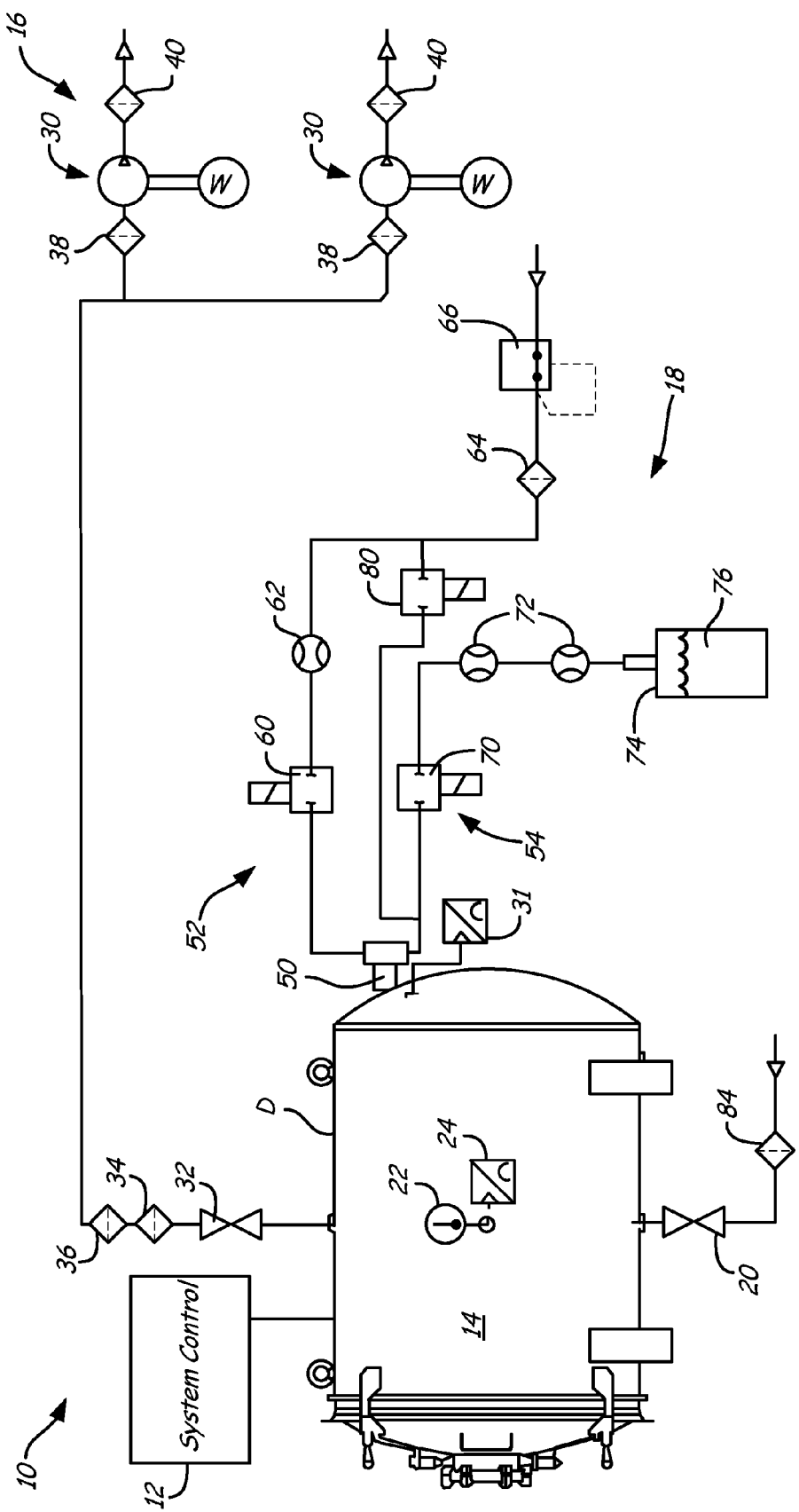
FIG. 1 is a schematic view of an embodiment of a system for decontaminating a medical device.

FIG. 1 is a schematic view of an embodiment of a system 10 for decontaminating a medical, dental, or other device. The system 10 includes a system controller 12, a decontamination chamber 14, a pressure control assembly 16, a chemical dispersion assembly 18, and a vent valve 20. The system controller 12 provides control signals to and/or receives control signals from components of the decontamination chamber 14, pressure control assembly 16, chemical dispersion assembly 18, and vent valve 20. In some embodiments, the system controller 12 is provided on the decontamination chamber 14 and is operatively connected to the components of the system 10. The system controller 12 may include an interface (e.g., on the decontamination chamber 14) that allows a user of the system 10 to provide inputs and receive information regarding operation of the system 10. For example, the system controller 12 may include an input device (e.g., a touch screen or keypad) that facilitates selection of decontamination cycle parameters by the user.

The decontamination chamber 14 is an enclosure that is fluidly connected to the pressure control assembly 16, chemical dispersion assembly 18, and vent valve 20. The device to be decontaminated is placed into the decontamination chamber 16 by opening the door D and placing the medical device on a rack or other supporting assembly in the interior of the decontamination chamber 16. When the door D is closed, the interior of the decontamination chamber 14 is sealed. The decontamination chamber 14 may include a temperature sensor 22 and a relative humidity sensor 24 configured to monitor environmental conditions in the decontamination chamber 14. In some embodiments, the decontamination chamber 16 includes a fluid connection that is couplable to the device being decontaminated, or to a package that encloses the device being decontaminated. For example, the decontamination chamber 16 may connect to the device and/or package similar to the system described in U.S. patent application Ser. No. 12/959,535, which is incorporated herein by reference in its entirety.

The pressure control assembly 16 includes one or more vacuum pumps 30 configured to evacuate the decontamination chamber 14 to produce a vacuum or partial vacuum in the decontamination chamber 14. In the embodiment shown, the pressure control assembly 16 includes two vacuum pumps 30. A vacuum control valve 32 is disposed between the decontamination chamber 14 and the vacuum pumps 30 and is configured to control fluid communication between the decontamination chamber 14 and the vacuum pumps 30. In an exemplary embodiment, the vacuum pumps 30 are configured to draw up to 300 liters per minute (L/min). A pressure transducer 31 may be operatively coupled to the decontamination chamber 14 to measure and monitor the pressure inside the decontamination chamber 14.

To destroy or neutralize decontaminating substances that are drawn from the decontamination chamber 14 during operation of the system 10, the pressure control assembly 16 includes one or more filters disposed between the vacuum control valve 32 and the vacuum pumps 30. In the embodiment shown, the pressure control assembly 16 includes filters 34, 36, 38 disposed between the vacuum control valve 32 and vacuum pumps 30. The type and number of filters employed in the pressure control assembly 16 may be a function of the type of decontaminating substance used in the system 10. For example, in some embodiments, the decontaminating substance includes hydrogen peroxide ($H_2O_2$), peracetic acid (PAA), and acetic acid. To neutralize this substance, the filter 34 may comprise potassium permanganate to remove the $H_2O_2$ and PAA, the filter 36 may comprise a particulate filter to remove particulate matter generated by the filter 34, and the filter 38 may comprise sodium bicarbonate to remove the acetic acid. In the embodiment shown, a filter 38 is associated with each vacuum pump 30. At the exit of the filters 38, the air drawn through the vacuum pumps 30 comprises oxygen ($O_2$) and carbon dioxide ($CO_2$). In some embodiments an exhaust filter 40 is connected to the outputs of each of the vacuum pumps 30.

The chemical dispersion assembly 18 disperses a decontaminating substance in the decontamination chamber 14 during operation of the system 10. The chemical dispersion assembly 18 includes a nozzle 50 connected to an air flow subassembly 52 and a chemical flow subassembly 54. The air flow subassembly 52 includes an air flow control valve 60, an air flow meter 62, an air filter 64, and an air pressure regulator 66. The air pressure regulator 66 may include a source of pressurized air. In an exemplary implementation, the air pressure regulator 66 provides pressurized air at about 50 pounds per square inch (psi). Air flow to the nozzle 50 is controlled by the air flow control valve 60 and monitored by the air flow meter 62. Air from the air pressure regulator 66 is filtered of impurities by the air filter 64.

The chemical flow subassembly 54 includes a chemical flow control valve 70, chemical flow meters 72, and chemical reservoir 74. Flow of a decontaminating fluid 76 from the chemical reservoir 74 to the nozzle 50 is controlled by the chemical flow control valve 70 and monitored by the chemical flow meters 72. The decontaminating substance may be pushed or pulled from the chemical reservoir 74. The chemical reservoir 74 may be a holding tank or other assembly configured to hold a decontaminating fluid 76. In some embodiments, the decontaminating fluid 76 is a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemical Indicators—Part I: General Requirements" (Arlington, VA: AAMI 2005). In some embodiments, the decontaminating fluid 76 is a room temperature (e.g, 20° C. to 25° C.) substance that can be dispersed as an atomized/vaporized solution or fog during the decontamination process. For example, the decontaminating fluid 76 may include $H_2O_2$, PAA, and/or acetic acid. The decontaminating fluid 76 may also be comprised of water. In one exemplary implementation, the decontaminating fluid 76 is comprised of about 62% water.

In some embodiments, the nozzle 50 is an atomizing nozzle that is configured to transform the decontaminating fluid 76 at the input of the nozzle 50 to a atomized/vaporized solution at the output of the nozzle 50. To produce the atomized/vaporized solution, the atomizing nozzle may generate fine droplets of the decontaminating fluid 76 that average, for example, less than about 10 µm in diameter or width. Droplets of this size tend to bounce off of solid surfaces, allowing for even dispersion, while avoiding excessive condensation, corrosion, and surface wetting issues in the decontamination chamber 14. In addition, the small droplets evaporate, and the vapor penetrates normally inaccessible areas, resulting in a more effective process. In some embodiments, the droplets of decontaminating fluid 76 are 10 µm diameter droplets with an evaporation rate of 50-375 ms at between 0-75% RH. One example nozzle 50 that may be suitable for use in the system 10 is a nozzle such as that used in the Minncare Dry Fog® or Mini Dry Fog systems, sold by Mar Cor Purification, Skippack, Pa. Another example nozzle 50 that may be suitable for use in the system 10 is a spray nozzle assembly including Spraying Systems Co. product numbers 1/4J-316SS, SU1A-316SS, and 46138-16-316SS, sold by Spraying Systems Co., Wheaton, Ill.

The amount of atomized/vaporized solution generated by the chemical dispersion assembly 18 is controlled by the system controller 12 by controlling the rate and amount of the decontaminating fluid 76 that is forced through the nozzle 50. The rate and amount of decontaminating fluid 76 that is forced through the nozzle 50 may be preprogrammed into the system controller 12 or may be manually entered into the system controller 12 by a user of the system 10. In addition, the system controller 12 may include multiple programs that provide different rates and amounts of the decontaminating fluid 76 to the nozzle 50.

In some embodiments, an atomizer purge valve 80 is connected between the air flow subassembly 52 and chemical flow subassembly 54. The atomizer purge valve 80 provides a fluid connection between the air pressure regulator 66 and the chemical flow subassembly 54 input to the nozzle 50. To purge decontaminating substance from the nozzle 50, the air control valve 60 and chemical control valve 70 are closed and the atomizer purge valve 80 is opened to allow pressurized air from the air pressure regulator 66 to be provided through the chemical input of the nozzle 50, thereby forcing residual decontaminating substance out of the nozzle 50.

The vent valve 20 allows air to be drawn into the decontamination chamber 14 during venting steps of the decontamination cycle. For example, if the pressure in the decontamination chamber 14 is below atmospheric pressure, the vent valve 20 may be opened to raise the pressure in the decontamination chamber 14. An air filter 84 is disposed along the intake to the vent valve 20 to remove contaminants from the air stream flowing into the decontamination chamber 14 during venting.

As discussed above, the system controller 12 operates the components of the system 10 to decontaminate a device or article in the decontamination chamber 14. The system controller 12 may include one or more selectable preprogrammed decontamination cycles that are a function of the device characteristics and desired level of decontamination. Alternatively, cycle parameters may be input into the system controller 12 by a user. As a part of the decontamination cycle, the system controller 12 may monitor and control the environment within the decontamination chamber 14 to improve the efficacy of the decontamination process. For example, the temperature, relative humidity, and pressure within the decontamination chamber 14 may be monitored via the temperature sensor 22, relative humidity sensor 24, and pressure sensor 31, respectively, that are operatively connected to the decontamination chamber 14. The system 10 may include a temperature control element (not shown) associated with the decontamination chamber 14 to control the temperature in the decontamination chamber 14. The pressure within the decontamination chamber 14 is controllable with the vacuum pumps 30, air pressure regulator 66, and vent valve 20.

Figure 2:
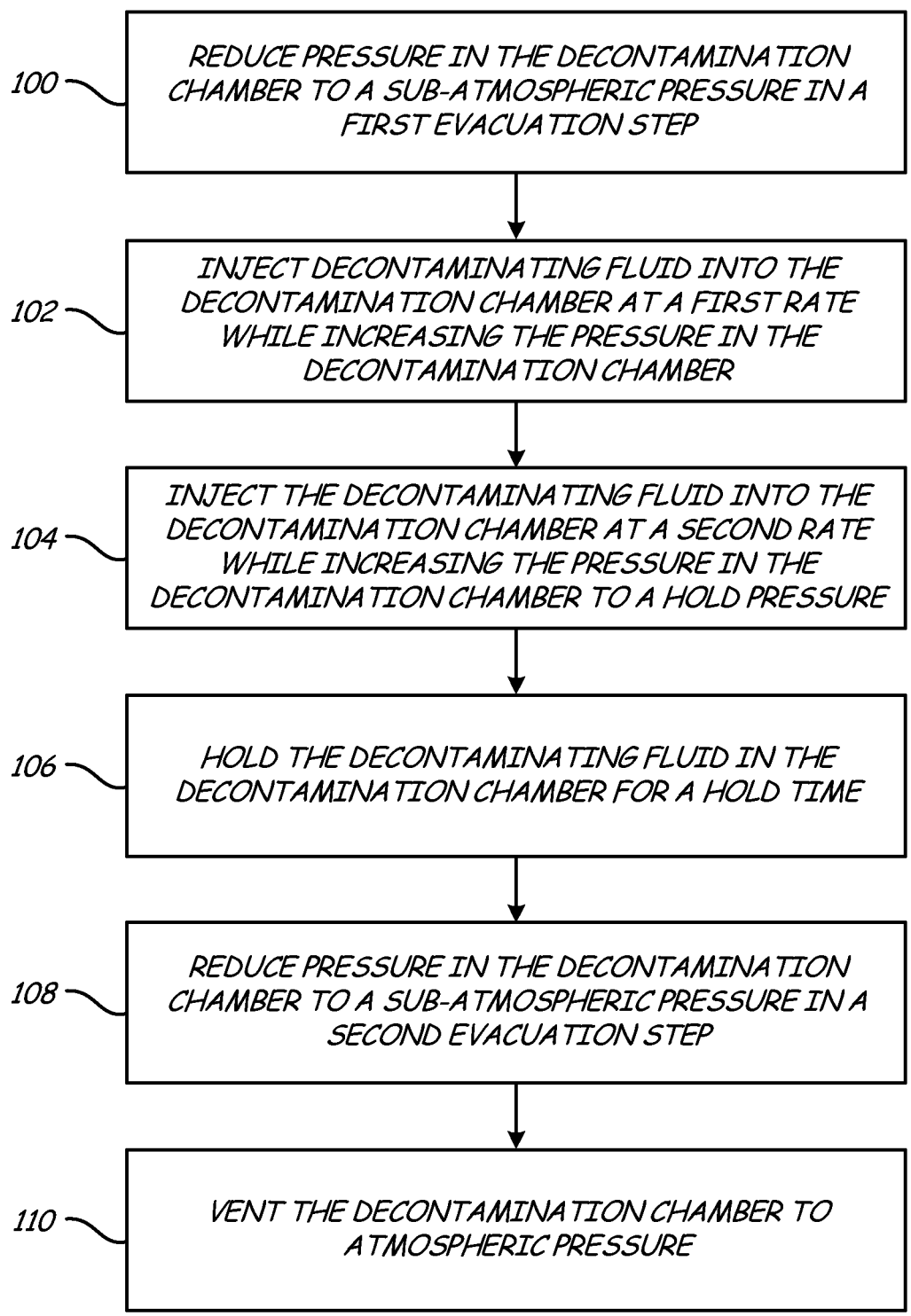
FIG. 2 is a flow diagram of an exemplary process for decontaminating a medical device in the system of FIG. 1.

FIG. 2 is a flow diagram of an embodiment of a process for decontaminating a device in the system 10 of FIG. 1. Prior to initiating the process, the device to be decontaminated may be preconditioned to allow the device to reach ambient temperature. In some embodiments, the ambient temperature is less than about 30° C., and more specifically between about 18° C. and about 30° C. The preconditioning of the device to ambient temperature improves the efficacy of the decontamination process of the system 10. The device to be decontaminated is placed inside the decontamination chamber 14, and the door D is closed to seal the interior of the decontamination chamber 14. In some embodiments, the relative humidity in the decontamination chamber 14 is preconditioned to less than about 50% relative humidity. The preconditioned relative humidity may be ambient relative humidity, or the conditions inside the decontamination chamber 14 may be adjusted to reach the preferred preconditioned relative humidity. The user may then initiate a decontamination cycle using the system controller 12.

In step 100, the pressure in the decontamination chamber is reduced to within a sub-atmospheric pressure range in a first evacuation step. For example, the pressure control assembly 16 may evacuate the decontamination chamber 14 to produce a vacuum or partial vacuum in the decontamination chamber 14. In some embodiments, the pressure in the decontamination chamber 16 is reduced to less than 10 torr.

After the pressure in the decontamination chamber 14 reaches the programmed sub-atmospheric pressure, the chemical dispersion assembly 18, in step 102, adds the decontaminating fluid 76 into the decontamination chamber 14 at a first rate. For example, the chemical dispersion assembly 18 may disperse or inject the decontaminating fluid 76 into the decontamination chamber 14. According to various embodiments, the first rate is selected such that the water content of the decontaminating fluid 76 increases the relative humidity and pressure in the decontamination chamber 14. As discussed above, the efficacy of the decontaminating fluid 76 may improve with higher relative humidity. In some embodiments, the decontaminating fluid 76 is dispersed at the first rate until the relative humidity is in the range of about 50% to about 90%. The relative humidity target is based on maximization of efficacy of the components of the decontaminating fluid 76.

While dispersing the decontaminating fluid 76, the pressure in the decontamination chamber 14 is increased. The pressure increase may be effected by the air pressure regulator 66 of the chemical dispersion assembly 18. That is, the air pressure that is employed to force the decontaminating fluid 76 through the nozzle 50 may be used to increase the pressure in the decontamination chamber 14. Alternatively, the pressure increase may be produced, at least in part, by opening the vent valve 20.

After the relative humidity in the decontamination chamber 14 reaches a preferred level, in step 104, the decontaminating fluid 76 is added into the decontamination chamber 14 at a second rate. In some embodiments, the second rate is higher than the first rate of step 102. The duration of adding at the second rate is set such that the concentration or density of the decontaminating fluid 76 reaches predetermined levels inside the decontamination chamber 14 at the end of dispersion at the second rate. The predetermined concentration of the decontaminating fluid 76 may be set in the decontamination cycle selected or programmed by the user on the system controller 12, and may be a function of the preferred or required level of decontamination of the device. The introduction of the decontaminating fluid 76 through the nozzle 50 with air flow subassembly 52 provides good circulation and coverage of the decontaminating fluid 76 within the decontamination chamber 14.

While the decontaminating fluid 76 is dispersed at the second rate, the pressure inside the decontamination chamber 14 is increased. Again, the pressure increase may be effected by the air pressure regulator 66 of the chemical dispersion assembly 18. Alternatively, the pressure increase may be produced, at least in part, by opening the vent valve 20. After adding the decontaminating fluid 76 at the second rate for a duration to produce the programmed level of concentration, the pressure inside the decontamination chamber 14 is within a hold pressure range. In some embodiments, the hold pressure is between about 1 and 760 torr. In a preferred embodiment, the hold pressure is about 500 torr.

In step 106, when the decontamination chamber 14 is within the hold pressure range, the conditions inside the decontamination chamber 14 are maintained for a hold time. The decontaminating fluid 76 is held in the decontamination chamber 14 for an amount of time sufficient to decontaminate the medical device disposed therein. This amount of time may be programmed into the system controller 12, and may be based on the size and type of medical device being decontaminated, as well as the content and concentration of the decontaminating fluid 76.

When the decontaminating fluid 76 has been held in the decontamination chamber 14 for the desired or programmed amount of time, in step 108, the system controller 12 commands the pressure control assembly 16 to again evacuate the decontamination chamber 14 to reduce the pressure in the decontamination chamber 14 to within a sub-atmospheric pressure range in a second evacuation step. The reduction in pressure draws the environment in the decontamination chamber 14 through the filters 34, 36, 38 and removes the decontaminating fluid 76 from the decontamination chamber 14. In some embodiments, the pressure in the decontamination chamber 14 is reduced to less than 10 ton. In some embodiments, the decontamination chamber 14 is maintained at the reduced pressure for a programmed period of time.

The steps of adding the decontaminating fluid 76 into the decontamination chamber 14 and/or evacuating the decontamination chamber 14 may be performed a plurality of times. For example, after the decontaminating fluid 76 is evacuated from the decontamination chamber 14 in a first cycle as described above, the decontaminating fluid 76 may be added into the decontamination chamber again in a second cycle. The decontaminating fluid 76 from the second cycle may then be held in the decontamination chamber 14 for a hold time (similar to step 106 described above). The decontamination chamber 14 may subsequently be evacuated to remove the decontaminating fluid 76, as described above in step 108. The system controller 12 may be programmed to repeat the decontamination cycle any number of times.

In addition, after any iteration of the second evacuation step, the system 10 may be programmed to increase the pressure in the decontamination chamber 14 without adding decontaminating fluid 76 into the chamber. For example, in some embodiments, the chemical flow control valve 70 is closed and the air flow control valve 60 is opened to force air into the decontamination chamber 14 to increase pressure. As another example, the vent valve 20 is opened to raise the pressure inside the decontamination chamber 14. After the pressure in the decontamination chamber 14 reaches a desired level (e.g., atmospheric pressure), the decontamination chamber 14 is again evacuated to a sub-atmospheric pressure. The additional steps of increasing pressure in the decontamination chamber 14 followed by evacuation may be employed to assure complete removal of the decontaminating fluid 76 from the decontamination chamber 14.

After the programmed number of cycles or evacuation steps, in step 110, the system controller 12 may open the vent valve 20 to vent the decontamination chamber 14 to atmospheric pressure. This draws air exterior to the decontamination chamber 14 through the air filter 84 and into the decontamination chamber 14. When the pressure in the decontamination chamber 14 equalizes with the pressure exterior of the decontamination chamber 14, the decontamination chamber 14 may be opened to remove the decontaminated device from the system 10.

Figure 3:
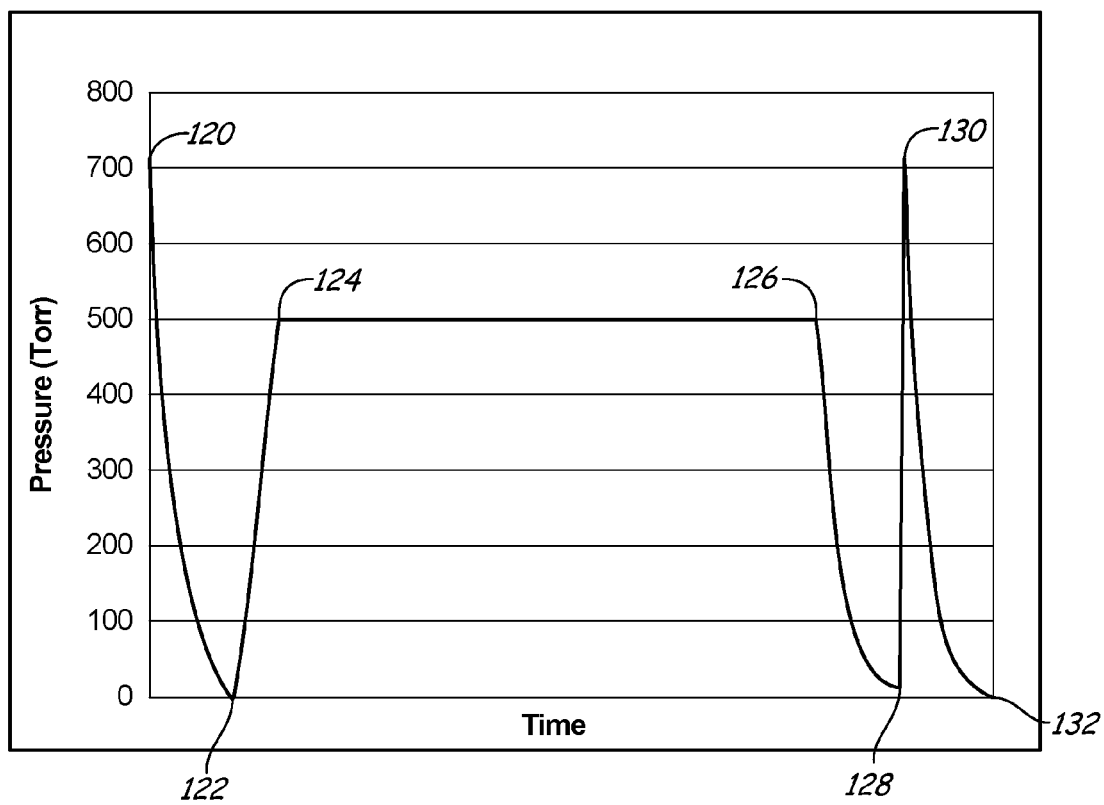
FIG. 3 is a graph of the relationship between pressure versus time during an exemplary decontamination cycle in the system of FIG. 1.

FIG. 3 is a graph of pressure versus time in an exemplary decontamination cycle. The graph in FIG. 3 illustrates the pressure conditions of the cycle after the device and decontamination chamber 14 have been preconditioned as described above. At time 120, the decontamination chamber 14 is evacuated to a sub-atmospheric pressure in a first evacuation step. In the embodiment shown, the sub-atmospheric pressure is approximately 10 ton. When the programmed sub-atmospheric pressure is reached in the decontamination chamber 14, at time 122, adding the decontaminating fluid 76 as described above in steps 102 and 104 occurs. After adding the decontaminating fluid 76 at the second rate as described in step 104, the decontamination chamber 14 is at the hold pressure at time 124. In the embodiment shown, the hold pressure is approximately 500 torr. The conditions in the decontamination chamber 14 are held constant for a hold time until time 126. In some embodiments, the hold time between times 124 and 126 is in the range of approximately five minutes to five hours. After the hold time, the decontamination chamber 14 is evacuated to a sub-atmospheric pressure in a second evacuation step. In the embodiment shown, the sub-atmospheric pressure is approximately 10 torr. When the programmed sub-atmospheric pressure is reached in the decontamination chamber 14, at time 128, the pressure is raised in decontamination chamber 14. In some embodiments, the pressure in the decontamination chamber is raised to approximately atmospheric pressure. After the programmed pressure is reached in the decontamination chamber 14, at time 130 the decontamination chamber 14 may again be evacuated to a sub-atmospheric pressure (e.g., 10 torr), and subsequently vented to atmospheric pressure at time 132. The additional evacuation step starting at time 130 is optional, and may be employed to assure complete removal of the decontaminating fluid 76 from the decontamination chamber 14.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A system for decontaminating a device, the system comprising:
   a decontamination chamber configured to retain the device;
   a chemical dispersion assembly configured to deliver a decontaminating fluid containing peracetic acid to the decontamination chamber;
   a pressure control assembly connected to the decontamination chamber and configured to control the pressure in the decontamination chamber; and
   a system controller configured to control the decontamination chamber, chemical dispersion assembly, and pressure control assembly to:
      add a decontaminating fluid into the decontamination chamber at a first rate while increasing the pressure in the decontamination chamber, wherein adding the decontaminating fluid increases a relative humidity in the decontamination chamber;
      following the addition of the decontaminating fluid at the first rate, add the decontaminating fluid into the decontamination chamber at a second rate higher than the first rate while increasing the pressure in the decontamination chamber to within a hold pressure range;
      hold the decontaminating fluid in the decontamination chamber for a hold time within the hold pressure range;
      evacuate the decontaminating fluid from the decontamination chamber in a decontaminating fluid evacuation step; and
      vent the decontamination chamber to atmospheric pressure after the decontaminating fluid evacuation step, wherein after the addition of the decontaminating fluid at the first rate and before the addition of the decontaminating fluid at the second rate, the relative humidity in the decontamination chamber is between about 50% and about 90%.

2. The system of claim 1, wherein the pressure control assembly reduces the pressure in the decontamination chamber to within a sub-atmospheric pressure after the decontaminating fluid is held in the decontamination chamber for a hold time and before the decontaminating fluid evacuation step.

3. The system of claim 1, wherein the chemical dispersion assembly comprises:
an atomizing assembly in fluid communication with the decontamination chamber.

4. The system of claim 3, wherein the atomizing assembly comprises:
an atomizing nozzle;
a chemical flow control system in fluid communication with the atomizing nozzle and a source of the decontaminating fluid; and
an air flow control system operatively connected to the atomizing nozzle, wherein the chemical flow control system is configured to deliver decontaminating fluid from the source of decontaminating fluid to the atomizing nozzle, and wherein the air flow control system is configured to force the decontaminating fluid through the atomizing nozzle.

5. The system of claim 1, and further comprising:
a neutralizing filter assembly coupled to the decontamination chamber such that decontaminating fluid in the decontamination chamber passes through the neutralizing filter assembly during the decontaminating fluid evacuation step.

6. The system of claim 1, wherein prior to adding the decontaminating fluid at a first rate the relative humidity in the decontamination chamber is less than about 50%.

7. The system of claim 1, wherein the system controller is configured to reduce a pressure in the decontamination chamber to within a sub-atmospheric pressure range prior to adding the decontaminating fluid into the decontamination chamber at the first rate.

8. A method for decontaminating a device in a decontamination chamber, the method comprising:
adding a decontaminating fluid into the decontamination chamber at a first rate while increasing the pressure in the decontamination chamber to a first pressure, wherein adding the decontaminating fluid increases a relative humidity in the decontamination chamber;
following the addition of the decontaminating fluid at the first rate, adding the decontaminating fluid into the decontamination chamber at a second rate higher than the first rate while increasing the pressure in the decontamination chamber from the first pressure to within a hold pressure range;
holding the decontaminating fluid in the decontamination chamber for a hold time within a hold pressure range;
evacuating the decontaminating fluid from the decontamination chamber in a decontaminating fluid evacuation step; and
venting the decontamination chamber to atmospheric pressure following the decontaminating fluid evacuation step, wherein after the addition of the decontaminating fluid at the first rate and before the addition of the decontaminating fluid at the second rate, the relative humidity in the decontamination chamber is between about 50% and about 90%.

9. The method of claim 8, further comprising reducing the pressure in the decontamination chamber to within a sub-atmospheric pressure range prior to adding the decontaminating fluid into the decontamination chamber at the first rate.

10. The method of claim 8, further comprising reducing the pressure in the decontamination chamber to within a sub-atmospheric pressure after the decontaminating fluid is held in the decontamination chamber for a hold time.

11. The method of claim 8, wherein during the decontaminating fluid evacuation step the decontaminating fluid in the decontamination chamber is forced through a neutralizing filter assembly.

12. The method of claim 8, and further comprising prior to adding the decontaminating fluid at the first rate, preconditioning the device to ambient temperature and the relative humidity in the decontamination chamber to less than about 50%.

13. A system for decontaminating a device, the system comprising:
a decontamination chamber configured to retain the device;
a chemical dispersion assembly configured to deliver a decontaminating fluid to the decontamination chamber, the chemical dispersion assembly comprising:
an atomizing nozzle;
a chemical flow control system in fluid communication with the atomizing nozzle and a source of the decontaminating fluid; and
an air flow control system operatively connected to the atomizing nozzle, wherein the chemical flow control system is configured to deliver decontaminating fluid from the source of decontaminating fluid to the atomizing nozzle, and wherein the air flow control system is configured to force the decontaminating fluid through the atomizing nozzle with forced air;
a pressure control assembly connected to the decontamination chamber and configured to control the pressure in the decontamination chamber; and
a system controller operably connected to the decontamination chamber, chemical dispersion assembly, and pressure control assembly, the system controller configured to:
control the chemical dispersion assembly to add a decontaminating fluid into the decontamination chamber at a first rate, wherein the forced air from the air control assembly increases the pressure in the decontamination chamber and the decontaminating fluid increases a relative humidity in the decontamination chamber;
following the addition of the decontaminating fluid at the first rate, control the chemical dispersion assembly to add the decontaminating fluid into the decontamination chamber at a second rate higher than the first rate while increasing the pressure in the decontamination chamber to about within a hold pressure range;
control the pressure control assembly to evacuate decontaminating fluid from the decontamination chamber after a hold time in a decontaminating fluid evacuation step; and
control the pressure control assembly to vent the decontamination chamber to atmospheric pressure, wherein after the addition of the decontaminating fluid at the first rate and before the addition of the decontaminating fluid at the second rate, the relative humidity in the decontamination chamber is between about 50% and about 90%.

14. The system of claim 13, wherein the pressure control assembly is configured to reduce the pressure in the decontamination chamber to within a sub-atmospheric pressure after the decontaminating fluid is held in the decontamination chamber for a hold time.

15. The system of claim 13, wherein the pressure control assembly is configured to reduce the pressure in the decontamination chamber to within a sub-atmospheric pressure prior to adding the decontaminating fluid into the decontamination chamber at the first rate.

16. The system of claim 13, and further comprising:
a neutralizing filter assembly coupled to the decontamination chamber such that decontaminating fluid in the decontamination chamber passes through the neutralizing filter assembly during the decontaminating fluid evacuation step.

17. The system of claim 16, wherein the neutralizing filter assembly comprises:
a first filter configured to neutralize a first component of the decontaminating fluid; and
a second filter connected in series with the first filter and configured to neutralize a second component of the decontaminating fluid.

18. The system of claim 13, wherein the device is preconditioned to an ambient temperature, and wherein prior to the decontaminating fluid addition step the relative humidity in the decontamination chamber is preconditioned to less than about 50%.

* * * * *